US008735608B2

(12) United States Patent
Zhang et al.

(10) Patent No.: US 8,735,608 B2
(45) Date of Patent: May 27, 2014

(54) PROCESS FOR PREPARING CARBONATE AND DIOL PRODUCTS

(75) Inventors: Xiankuan Zhang, Houston, TX (US); Ray Montez, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 18 days.

(21) Appl. No.: 13/406,728

(22) Filed: Feb. 28, 2012

(65) Prior Publication Data

US 2013/0225840 A1 Aug. 29, 2013

(51) Int. Cl.
*C07D 317/38* (2006.01)
*C07C 68/06* (2006.01)

(52) U.S. Cl.
USPC ......................................... 549/230; 558/277

(58) Field of Classification Search
USPC .......................................... 549/230; 558/277
See application file for complete search history.

(56) References Cited

U.S. PATENT DOCUMENTS

| | | | |
|---|---|---|---|
| 4,691,041 | A | 9/1987 | Duranleau et al. |
| 5,359,118 | A | 10/1994 | Wagner et al. |
| 5,648,508 | A | 7/1997 | Yaghi |
| 6,407,279 | B1 | 6/2002 | Buchanan et al. |
| 6,479,689 | B1 | 11/2002 | Tojo et al. |
| 6,617,467 | B1 | 9/2003 | Muller et al. |
| 6,624,318 | B1 | 9/2003 | Muller et al. |
| 7,084,292 | B2 | 8/2006 | Buchanan et al. |
| 7,119,219 | B2 | 10/2006 | Mueller et al. |
| 7,435,842 | B2 | 10/2008 | Miyake et al. |
| 7,446,218 | B2 | 11/2008 | Miyake et al. |
| 7,556,673 | B2 | 7/2009 | Schubert et al. |
| 7,652,122 | B2 | 1/2010 | Miyake et al. |
| 7,663,005 | B2 | 2/2010 | Crudge et al. |
| 7,842,827 | B2 | 11/2010 | Schubert et al. |
| 7,879,221 | B2 | 2/2011 | Putter et al. |
| 7,880,026 | B2 | 2/2011 | Ni et al. |
| 7,910,732 | B2 | 3/2011 | Schubert et al. |
| 7,968,739 | B2 | 6/2011 | Mueller et al. |
| 2003/0023109 | A1 | 1/2003 | Schlosberg et al. |

FOREIGN PATENT DOCUMENTS

| | | |
|---|---|---|
| CN | 10147456 A | 8/2009 |
| EP | 1125915 A1 | 8/2001 |
| JP | 2003342233 A | 12/2003 |
| WO | 2008129030 A1 | 10/2008 |

OTHER PUBLICATIONS

Song, J., Zhang, et al., Synthesis of cyclic carbonates and dimethyl carbonate using CO2 as a building block catalyzed by MOF-5/KI and MOF-5/KI/K2CO, Frontiers of Chemistry in in China 6 (1), Mar. 2011, pp. 21-30.
Song, J., Zhang, Z., Hu, S., Wu, T., Jiang, T., Han, B., "MOF-5/n-Bu4NBr: An efficient catalyst system for the synthesis of cyclic carbonates from epoxides and CO2 under mild conditions", Green Chemistry, vol. 11, Issue 7, 2009, pp. 1031-1036.
Zhou, Y., Song, J., Liang, S., Hu, S., Liu, H., Jiang, T., Han, B., "Metal-organic frameworks as an acid catalyst for the synthesis of ethyl methyl carbonate via transesterification", Journal of Molecular Catalysis A: Chemical 308 (1-2), Aug. 2009, pp. 68-72.
Li, Y., Tang, Z.-G., Zhu, J.-Q., Fei, W.-Y. , "CO2 solubility in dimethyl carbonate and its intensification approaches", Huaxue Gongcheng/Chemical Engineering (China) 38 (8), Aug. 2010, pp. 69-72 (English Abstract Only).
Chang, Y., Jiang, T., Han, B., Liu, Z., Wu, W., Gao, L., Li, J., Gao, H., Zhao, G., Huang, J., "One-pot synthesis of dimethyl carbonate and glycols from supercritical CO2, ethylene oxide or propylene oxide, and methanol", Applied Catalysis A: General, vol. 263, Issue 2, Jun. 10, 2004, pp. 179-186.
Song, J., Zhang, Z., Han, B., Hu, S., Li, W., Xie, Y., "Synthesis of cyclic carbonates from epoxides and CO2 catalyzed by potassium halide in the presence of β-cyclodextrin", Green Chemistry vol. 10, Issue 12, 2008, pp. 1337-1341.
Liang, S., Liu, H., Jiang, T., Song, J., Yang, G., Han, B., "Highly efficient synthesis of cyclic carbonates from CO2 and epoxides over cellulose/KI", Chemical Communications vol. 47, Issue 7, Feb. 21, 2011, pp. 2131-2133.
Jiang, J.-I., Hua, R., "Synthesis of Dimethyl Carbonate from CO2, Methanol, and Epoxides Using Re(CO)5 CI/K2 CO3 as Catalyst System", Chemical Research in Chinese Universities vol. 23, Issue 3, May 2007, pp. 374-376.
Song, Z., La, G.-H., Yu, Y., Shi, Z., Feng, S.-H., "Hydrothermal Synthesis and Structural Characterization of Three-dimensional Metal-organic Framework [Zn3(C2H2N3)2(C7H5O2)4]", Chemical Research in Chinese Universities, vol. 25, Issue 1, 2009, pp. 1-4.
Tian, J.-S., Miao, C.-X., Wang, J.-Q., Cai, F., Du, Y., Zhao, Y., He. L.-N., "Efficient synthesis of dimethyl carbonate from methanol, propylene oxide and CO2 catalyzed by recyclable inorganic base/phosphonium halide-functionalized polyethylene glycol", Green Chemistry, vol. 9, Issue 6, 2007, pp. 566-571.
IonPac® AS21 Anion-Exchange Column Information Sheet, Dionex Corporation, Copyright Date Listed 2005, pp. 1-4.
Purolite Ion Exchange Resin Technical Data Sheet, no date listed, accessed Feb. 23, 2012, pp. 1-8.

(Continued)

*Primary Examiner* — Kristin Vajda
(74) *Attorney, Agent, or Firm* — Cantor Colburn LLP

(57) ABSTRACT

A method of forming a cyclic carbonate product is carried out by reacting an alkylene oxide, such as ethylene oxide, with carbon dioxide in the presence of a metal organic framework (MOF) catalyst with less than 0.5 mol % of any potassium or quaternary ammonium salts present based on moles of alkylene oxide feed in a reaction zone under reaction conditions to form a cyclic carbonate product. The cyclic carbonate product may be optionally fed as a crude carbonate product that does not undergo any purification or separation, other than the optional removal of any portion of unreacted alkylene oxide, carbon dioxide, and light hydrocarbon gases, to a second reaction zone containing a transesterification catalyst along with an aliphatic monohydric alcohol. The cyclic carbonate product and monohydric alcohol are allowed to react under reaction conditions to form the dialkyl carbonate and diol products.

26 Claims, 1 Drawing Sheet

(56) References Cited

OTHER PUBLICATIONS

Carreon, Moises A., "Metal organic frameworks as catalysts in the conversion of CO2 to cyclic carbonates", Indian Journal of Chemistry, vol. 51A, Sep.-Oct. 2012, 1306-1314.

Cho, Hye-Young, et al., "CO2 adsorption and catalystic application of Co-MOF-74 synthesized by microwave heating", Catalysis Today 185 (2012) 35-40.

Chui, Stephen S.-Y. et al., "A Chemically Functionalizable Nanoporous Material [Cu 3(TMA)2(H2O)3]n", Science, vol. 283 (Feb. 19, 1999) 1148-1150.

International Search Report for PCT/US2012/067526 (SB20022PCT) mailed Mar. 20, 2013, 9 pages.

Macias, Eugenia E., et al., "Catalytic activity of metal organic framework Cu3 (BTC)2 in the cycloaddition of CO2 to epichlorohydrin reaction", Catalysis Today, 198 (2012) 215-218.

Miralda, Carmen M., et al., "Zeolitic Imidazole Framework-8 Catalysts in the Conversion of CO2 to Chloropropene Carbonate", ACS Catalysis, American Chemical Society, US, vol. 2, Jan. 1, 2012, 180-183.

Nakhla, Josephine, "Metal Organic Frameworks (MOFs)", Adrich ChemFlles, Jan. 1, 2009, 3 pages.

Park, Sung Kyo, et al., "Exeptional chemical and thermal stability of zeolitic imidazolate frameworks", Proceedings of the National Academy of Science (PNAS), Jul. 5, 2006, vol. 103, No. 27, 10186-10191.

Written Opinion of the International Searching Authority for PCT/US2012/067526 (SL mailed 14 pages, 2013.

Zhou, Xi, et al., "Funchtionalized IRMOF-3 as efficient heterogeneous catalyst for the synthesis of cyclic carbonates", Journal of Molecular Catalysis A: Chemical, 361-362 (2012) 12-16.

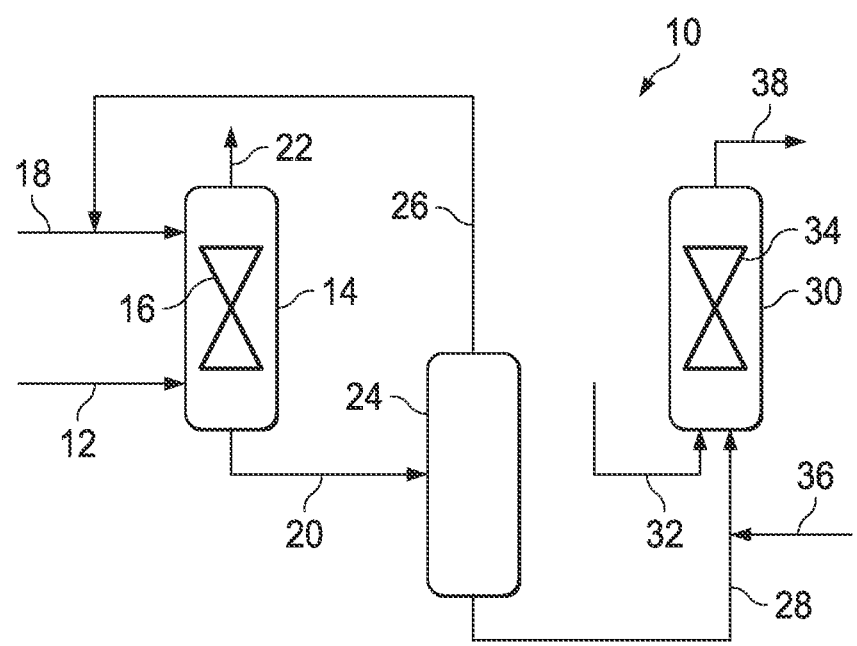

PROCESS FOR PREPARING CARBONATE AND DIOL PRODUCTS

FIELD OF THE INVENTION

The present invention relates to methods for preparing carbonate and diol products from alkylene oxide.

BACKGROUND

Monoethylene glycol (MEG), often referred to as ethylene glycol, is an important compound that is often used in antifreeze and in the production of certain polymers, such as polyester and polyethylene terephthalate, which is commonly used in plastic bottles for soft drinks. Ethylene glycol may be produced by the reaction of ethylene oxide and water. Various byproducts, such as di-ethylene glycol (DEG), tri-ethylene glycol (TEG), etc., are often co-produced using this synthesis method, so that yields of monoethylene glycol may be lower than desired. As used herein, the expression "ethylene glycol" without any prefix is meant to encompass monoethylene glycol, unless otherwise stated or is apparent from its context.

Another method of forming ethylene glycol is from ethylene carbonate (EC). Ethylene carbonate may be converted to dimethyl carbonate (DMC) and ethylene glycol in the presence of methanol in a transesterification reaction. Using such reaction method, the yield of ethylene glycol is much higher, with less undesirable byproducts being produced. Additionally, the product dimethyl carbonate produced in such reaction is useful as an oxygenate additive in fuel and in the production of Bisphenol A, which is commonly used in making polycarbonate plastics and epoxy resins.

The ethylene carbonate used in producing ethylene glycol and dimethyl carbonate may be prepared from ethylene oxide in a carbonation reaction. The carbonation of ethylene oxide with carbon dioxide ($CO_2$) yields ethylene carbonate. The use of carbon dioxide as a reactant may be particularly desirable due to the increased emphasis presently placed on minimizing $CO_2$ emissions.

To yield ethylene glycol in the transesterification reaction, a purified source of ethylene carbonate is typically used. Recently, however, integrated processes have been developed that utilize ethylene oxide and $CO_2$ in a first carbonation stage to yield a crude or unpurified ethylene carbonate product, which is then used in a second transesterification stage wherein the ethylene carbonate product is converted to ethylene glycol and dimethyl carbonate.

Although an integrated process eliminates the need for a purified ethylene carbonate source, one of the issues with an integrated process is the effect of the catalyst used in the carbonation reaction on the transesterification reaction.

Homogeneous catalysts are often used for the carbonation reaction. Such homogeneous catalysts may include potassium and quaternary ammonium halide salts, such as those described in U.S. Pat. No. 7,084,292. Without purification of the ethylene carbonate product to remove the homogeneous catalyst, the homogeneous catalyst is carried with the ethylene carbonate product into the reaction zone used for transesterification. For ion exchange resins (IER) catalysts, which are often used in the transesterification reactions, the IER catalyst may tend to absorb the halide ions of the homogeneous carbonation catalysts. Such absorption of halide ions of the homogeneous carbonation catalyst may tend to decrease the effectiveness of the IER transesterification catalyst.

Accordingly, improvements are needed to provide an integrated carbonation/transesterification process for the production of ethylene glycol and/or dimethyl carbonate, and similar products, which overcomes these and other issues.

SUMMARY

A method of forming an ethylene carbonate product is conducted by reacting ethylene oxide with carbon dioxide in the presence of a metal organic framework (MOF) catalyst with less than 0.5 mol % of any potassium or quaternary ammonium salts present based on moles of ethylene oxide feed in a reaction zone under reaction conditions to form the ethylene carbonate product.

In particular embodiments, the MOF catalyst may be at least one selected from aluminum terephthalate ($C_8H_5AlO_5$), copper benzene-1,3,5-tricarboxylate ($C_{18}H_6Cu_3O_{12}$), and 2-methylimidazole zinc salt ($C_8H_{12}N_4Zn$). The MOF catalyst may be used in an amount to provide a LHSV of from 0.5 $hr^{-1}$ to 10 $hr^{-1}$.

In certain embodiments, the ethylene carbonate product is a crude ethylene carbonate product and the method further includes feeding the crude ethylene carbonate product from the reaction zone in an integrated process to a second reaction zone. In such an integrated process, the crude ethylene carbonate product does not undergo any purification or separation, other than the optional removal of any portion of unreacted ethylene oxide, carbon dioxide or light hydrocarbon gases. The second reaction zone contains a transesterification catalyst along with an aliphatic monohydric alcohol. The ethylene carbonate product and monohydric alcohol are allowed to react under reaction conditions to form dialkyl carbonate and diol products.

In certain embodiments of the integrated process, the aliphatic monohydric alcohol is a $C_1$ to $C_5$ aliphatic monohydric alcohol. In particular embodiments, the monohydric alcohol may be methanol and the dialkyl carbonate may include dimethyl carbonate and the diol may include monoethylene glycol.

The transesterification catalyst of the integrated process may be at least one of an MOF catalyst, an ion exchange resin, and a homogeneous catalyst. In more particular embodiments, the transesterification catalyst is an MOF catalyst.

In some embodiments of the integrated process the molar ratio of aliphatic monohydric alcohol to the crude ethylene carbonate product introduced into the second reaction zone is from 1.5:1 to 3:1.

Where the transesterification catalyst is an ion exchange resin, the ion exchange resin may be a strongly basic Type I ion exchange resin in gel form of polystyrene crosslinked with divinyl benzene having from 4% to 8% crosslinking, and from 40% to 60% water retention. The ion exchange resin may include at least one of quaternary ammonium groups or quaternary phosphonium groups and be configured as substantially spherical beads having a particle size of from 0.2 mm to 1.5 mm. In particular embodiments, the ion exchange resin may include an anion selected from the group consisting of bicarbonate, bisulfite, metalate, carboxylate, and halide.

In another aspect of the invention, a method of forming dialkyl carbonate and diol products in an integrated process includes reacting an alkylene oxide with carbon dioxide in the presence of a metal organic framework (MOF) catalyst with less than 0.5 mol % of any potassium or quaternary ammonium salts present based on moles of alkylene oxide feed present in a first reaction zone under reaction conditions to form a crude cyclic carbonate product. The crude cyclic carbonate product from the first reaction zone is fed to a second reaction zone. The crude carbonate product does not undergo any purification or separation, other than the optional removal of any portion of unreacted alkylene oxide, carbon dioxide, and light hydrocarbon gases. The second reaction zone contains a transesterification catalyst along with an aliphatic monohydric alcohol. The cyclic carbonate product and monohydric alcohol are allowed to react under reaction conditions to form the dialkyl carbonate and diol products.

In certain embodiments, the alkylene oxide has the formula

wherein $R_1$ and $R_2$ are independently from one another a $-(CH_2)_m-$ group, wherein m is an integer of from 1 to 3, more particularly 1 to 2. In particular embodiments, the alkylene oxide may be ethylene oxide and the cyclic carbonate product may be ethylene carbonate.

In particular instances, the MOF catalyst may be used in the first reaction zone in an amount to provide a LHSV of from 0.5 hr$^{-1}$ to 10 hr$^{-1}$. In some embodiments, the MOF catalyst is at least one selected from aluminum terephthalate ($C_8H_5AlO_5$), copper benzene-1,3,5-tricarboxylate ($C_{18}H_6Cu_3O_{12}$), and 2-methylimidazole zinc salt ($C_8H_{12}N_4Zn$).

In some cases, the aliphatic monohydric alcohol may be a $C_1$ to $C_5$ aliphatic monohydric alcohol, and in particular the monohydric alcohol may be methanol. Where the aliphatic monohydric alcohol is methanol, the alkylene oxide may be ethylene oxide, the dialkyl carbonate may include dimethyl carbonate, and the diol may include monoethylene glycol.

In the integrated process, the transesterification catalyst may be at least one of an MOF catalyst, ion exchange resin, and a homogeneous catalyst. In particular embodiments, the transesterification catalyst is an MOF catalyst. In the transesterification, the molar ratio of aliphatic monohydric alcohol to the crude cyclic carbonate product introduced into the second reaction zone may be from 1.5:1 to 3:1.

In certain embodiments, the transesterification catalyst is a strongly basic Type I ion exchange resin in gel form of polystyrene crosslinked with divinyl benzene having from 4% to 8% crosslinking, and from 40% to 60% water retention. The ion exchange resin may include at least one of quaternary ammonium groups or quaternary phosphonium groups and be configured as substantially spherical beads having a particle size of from 0.2 mm to 1.5 mm. The ion exchange resin may include an anion selected from the group consisting of bicarbonate, bisulfite, metalate, carboxylate, and halide.

In other embodiments, the transesterification catalyst may be a strongly basic homogeneous catalyst having a pKa value of 5 or more.

BRIEF DESCRIPTION OF THE DRAWINGS

For a more complete understanding of the present invention, and the advantages thereof, reference is now made to the following descriptions taken in conjunction with the accompanying figures, in which:

FIG. 1 is a schematic of integrated process system for producing dimethyl carbonate and ethylene glycol from ethylene oxide and carbon dioxide starting materials using a MOF carbonation catalysts and a transesterification catalyst.

DETAILED DESCRIPTION

In preparing cyclic carbonate products, alkylene oxide is reacted with carbon dioxide in a carbonation reaction. As well be described later on, the cyclic carbonate products may then be optionally used in the production of dialkyl carbonate and diol products in an integrated process according to the invention. In many applications the alkylene oxide will be ethylene oxide, which is then used to prepare ethylene carbonate in the carbonation reaction. The alkylene oxide may include other compounds, such as propylene oxide, however. Other alkylene oxides may also be used for the preparation of cyclic carbonate products and subsequent dialkyl carbonate and diol products. Generally, the alkylene oxide may have the Formula (1) below:

(1)

wherein $R_1$ and $R_2$ are independently from one another a $-(CH_2)_m-$ group, wherein m is an integer of from 1 to 3, more particularly 1 to 2.

In the carbonation reaction, the alkylene oxide is reacted with carbon dioxide ($CO_2$) in a carbonation reactor to form the cyclic carbonate product. The reaction may be illustrated by the following Equation (2) below:

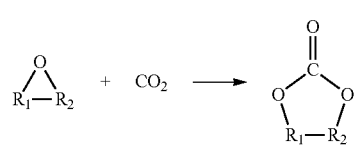

(2)

wherein $R_1$ and $R_2$ are the same as described for Formula (1). The above reaction constitutes the carbonation reaction and also shows the stoichiometric numbers for the reaction and the cyclic carbonation product.

The carbon dioxide used in the carbonation may be a purified carbon dioxide source, however, other non-purified sources of carbon dioxide may be used. Impurities in such non-purified carbon dioxide source may include nitrogen, oxygen, hydrogen, carbon monoxide, nitric oxide, and light hydrocarbons. The carbon dioxide may be used in approximately stoichiometric amount with the alkylene oxide. In many instances an excess of carbon dioxide may also be used with a $CO_2$/alkylene oxide molar feed ratio ranging from greater than 1 to about 2. The amount of carbon dioxide used in the carbonation may be adjusted as necessary to provide the optimum reaction performance and conversion. Additionally, the carbon dioxide feed used in the carbonation reaction may be, at least in part, a recycled carbon dioxide, as is described later on.

It should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

In the present invention, the carbonation catalyst is a metal organic framework (MOF) catalyst. Such catalysts have been found to be active and selective for the formation of cyclic carbonate products. MOF catalysts are solid materials that remain in the carbonation reactor so that they are not carried in the reactor effluent. There is therefore no need to separate the catalyst from the reaction effluent and the MOF materials do not impact any downstream operation, including the transesterification catalyst and reaction. MOF materials do not dissolve in the carbonation reaction feeds described herein, and therefore can be used as a heterogeneous catalyst. They are also thermally stable at temperatures up to 400° C. or higher, some of them up to as high as 500° C.

Structurally, the MOF compounds are crystalline structures formed from metal ions or metal ion clusters that act as joints or are coordinated or bound by multidirectional organic molecules or ligands that provide a network in the form of a crystalline structure. These networks may be one-dimensional (1-D), two-dimensional (2-D) or three-dimensional (3-D) extended, periodic structures. The structural network is formed in such a way that regular arrays are formed resulting in robust (often porous) materials that are analogous to zeolites. They have an extremely high surface area, typically from about 1000 m²/g or more, with some of them having surface areas of over 10,000 m²/g. Most porous MOFs are microporous, having pore diameters of less than about 2 nm. These typically provide the highest surface areas. A limited number of mesoporous MOFs have also been developed having pore diameters of from 2 to 50 nm. The surface chemical properties may be modified depending upon the actual applications. Particularly useful in the reactions described herein are those MOFs having surface basicity.

Such MOF materials are well known and have been described, for instance, in U.S. Pat. Nos. 5,648,508; 6,617476; 6,624,318; 6,624,318; 7,556,673; 7,842,827; 7,879,221; 7,880,026; 7,910,732, and 7,910,732, each of which is herein incorporated by reference in its entirety for all purposes. Various metals may be used as the metal ion for the MOF, such as aluminum (Al), copper (Cu), iron (Fe), and zinc (Zn). Different organic linkers may also be used, such as 1,4-benzenedicarboxylate (BDC), benzene-1,3,5-tricarboxylic acid (BTC), and 2-methylimidazole. Non-limiting examples of particularly useful MOF catalysts include aluminum terephthalate ($C_8H_5AlO_5$), copper benzene-1,3,5-tricarboxylate ($C_{18}H_6Cu_3O_{12}$), and 2-methylimidazole zinc salt ($C_8H_{12}N_4Zn$).

The MOF carbonation catalyst may be used with or without the presence of other catalysts. In certain applications, the MOF carbonation catalyst may be used without the presence of any homogeneous catalysts. In particular, MOF carbonation catalyst may be used without the presence of potassium and quaternary ammonium halide salts, or other halide salts. If such salts are present they may be present in low amounts of less than 1.0 mol %, 0.5 mol %, 0.4 mol %, 0.3 mol %, 0.2 mol %, 0.1 mol %, 0.05 mol %, or 0.01 mol % based on moles of alkylene oxide feed.

The carbonation reaction can be carried out in a variety of different reactors, batch or continuous. These reactors may include stir tank, plug flow, fluidized bed, reactive distillation type reactors, etc. One or more reactors, used in series or parallel, may be used for the carbonation reactions. The MOF carbonation catalyst is typically used in an amount to provide a LHSV of from about 0.5 $hr^{-1}$ to about 10 $hr^{-1}$, more particularly from about 2 $hr^{-1}$ to about 6 $hr^{-1}$.

Typical carbonation reaction conditions include a temperature range of from about 50° C. to about 250° C., with from about 120° C. to about 220° C. being more typical. Reactor pressures may range from about 100 to about 1000 psig, more particularly from about 200 to about 500 psig. Carbon dioxide is typically introduced into the reactor separately from the alkylene oxide and catalyst.

The carbonation reaction products include the cyclic carbonate product, as shown in Equation (2), along with other compounds and byproducts. These may include any unreacted alkylene oxide and carbon dioxide, as well as other impurities. Byproducts in the reactor effluent may include ethylene glycol, di- and tri-ethylene glycol, and higher glycols. This is particularly true in cases where water is present during the reaction, such as that may be present in any unpurified alkylene oxide feed.

In a non-integrated process where the cyclic carbonation product is later used in a transesterification process to produce dialkyl carbonate and diol products, the impurities are typically removed from the cyclic carbonate product prepared in the carbonation reaction. In the present invention directed to an integrated process, however, the crude cyclic carbonate product from the carbonation reaction may be used in a transesterification stage without any purification, other than the optional separation or removal of any portion of unreacted alkylene oxide, carbon dioxide, and/or light hydrocarbon gases. Accordingly, as used herein, the expression "integrated process" and similar expressions are meant to encompass those processes wherein the carbonation products initially prepared in such process are then used in the transesterification process or stage without any separation of byproducts or impurities, other than the optional separation or removal of unreacted alkylene oxide and carbon dioxide that can be readily removed without substantial processing or interruption of a continuous process flow. While the integrated process is particularly useful in a continuous flow process, wherein the carbonation reactor effluent is fed on continuous or substantially continuous basis to the transesterification reactor or reaction zones, it should be apparent to those skilled in the art, that temporary collection and storage of the carbonation products may still be used such that the process is not generally continuous. The integrated process is therefore also meant to encompass those non-continuous processes wherein the carbonation products may be temporarily collected and stored for a period of time, provided the carbonation products are crude carbonation products that are then used in the transesterification process, with only optional removal of the aforementioned alkylene oxides and carbon dioxide.

In the integrated process, after carbonation, the crude cyclic carbonation product is further processed in a transesterification stage, wherein the cyclic carbonation product is converted to dialkyl carbonate and diol products. Typically a reagent of an aliphatic monohydric alcohol is used in the transesterification. The alcohol is typically an alcohol having a $C_1$ to $C_5$ alkyl group. The transesterification reaction is represented in stoichiometric amounts by Equation (3) below:

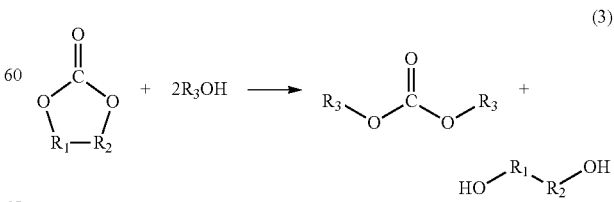

(3)

wherein $R_1$ and $R_2$ are the same as defined previously with respect to Formula (1), and $R_3$ is a $C_1$ to $C_5$ alkyl group.

Various transesterification catalysts may be used in the integrated process. These may include homogeneous, IER and MOF catalysts. With respect to the homogeneous transesterification catalyst, the catalyst is in the same phase as the transesterification reactants. Various homogeneous catalysts are known for the transesterification of cyclic carbonates to form dialkyl carbonates and diols. These may include certain hydrides, oxides, hydroxides, methoxides, alcoholates, amides, carbonates, amides, and salts of alkali metals and alkaline earth metals. Particularly useful alkali metals are lithium, sodium, potassium, and cesium, and more particularly sodium and potassium. Such homogeneous transesterification catalysts are described, for example, in U.S. Pat. Nos. 5,359,118; 6,479,689; and 7,084,292, each of which is incorporated herein by reference for all purposes. Non-limiting specific examples of useful homogeneous catalysts include KOH, $KHCO_3$, $K_2CO_3$, NaOH, $Na_2CO_3$, and $NaHCO_3$.

Particularly useful as homogeneous transesterification catalysts are those that are strongly basic. Such strong base catalysts include the alkali hydroxides, methoxides and carbonates. In particular, those homogeneous catalysts having pKa values of from 5 or more, particularly from about 6, 7, 8, 9, 10, 11, 12, 13, 14, 15 or higher. Those catalysts with a higher pKa value tend to be more active in the transesterification reaction. Thus, for example, KOH and $KOCH_3$ were found to be the most active transesterification catalysts, while $K_2CO_3$ was less active and $KHCO_3$ was even less active. This correlates with their respective pKa values, as presented in Table 1 below:

TABLE 1

| Catalyst | M.W. | pKa |
|---|---|---|
| KOH | 56.11 | 14 |
| $KHCO_3$ | 100.12 | 6.35 |
| $K_2CO_3$ | 138.21 | 10.33 |
| $KOCH_3$ | 70.13 | 15.5-16 |

The homogeneous catalysts are typically dissolved in the cyclic carbonate and/or monohydric alcohol feed. The homogeneous catalyst may also be introduced separately into the reaction zone.

Ion exchange resin catalysts may also be used for the transesterification reaction. Such IER catalysts are known for the transesterification reaction for converting cyclic carbonates to dialkyl carbonate and diol products. Such IER resins are described, for example in U.S. Pat. Nos. 4,691,041 and 6,479,689; U.S. Pat. App. Pub. No. US2003/0023109A1 and EP1125915B1, each of which is incorporated herein by reference in its entirety for all purposes.

The ion exchange resins may be strongly basic anion exchange resins or strongly acidic cation exchange resins. In certain applications, however, strong base anion exchange resins may be used, as acid resins have been found to be less selective and may have a shorter life than their base counterpart resins in transesterification.

In one particular embodiment, specialized ion exchange resin catalysts may be used in the transesterification reaction. The ion exchange resin catalyst is a strongly basic (anionic) ion exchange resin that is a heterogeneous catalyst wherein the basic groups are quaternary ammonium or quaternary phosphinium. Anionic ion exchange resins are typically classified as strongly basic or weakly basic. Strongly basic anions include anions such as $Cl^-$ and $SO_4^-$. Strongly basic anion ion exchange resins that have quaternary ammonium or phosphium groups as the exchanging group dissociate in the same way as strong alkalis such as NaOH and KOH and exhibit strong basicity. The quaternary ammonium exchange group of such resins are so strongly basic that they dissociate into $R—N^+OH^-$ not only in acidic but even in alkaline solutions. They have ion exchange properties over the entire pH range.

The strongly basic ion exchange resins may include those classified as Type I and Type II. Type I are those with a trimethylammonium group (($R—N^+(CH_3)_3$). Type II are those with a dimethylethanolammonium group ($R—N^+(CH_3)_2CH_2CH_2OH$).

The ion exchange resins may be based on the copolymer of styrene and divinylbenzene, vinylpryidine, polysiloxanes, as well as other solid supports having electropositive complexing sites of an inorganic nature, such as carbon, silica, silicaalumina, zeolites, glass and clays, such as hydrotalcite. Further, immobilized complexing macrocycles such as crown ethers, etc. can be used as well as a solid support. Such ion exchange resins are described in U.S. Pat. No. 7,663,005, which is incorporated herein by reference for all purposes.

Particularly useful are those ion exchange resin catalysts that are based on a strongly basic quaternary ammonium resin that includes polystyrene that is crosslinked with divinyl benzene. The divinyl benzene in such catalysts is present in an amount of from about 2 to about 10% by weight, more particularly from about 4 to about 8% by weight, wherein the polystyrene is crosslinked with from about 4 to about 8% by weight of divinyl benzene.

The ion exchange resin employed in the present invention typically includes basic groups that are bonded to the crosslinked polystyrene resin. The basic groups that are bonded to the crosslinked polystyrene resin include quaternary ammonium or quaternary phosphonium, with quaternary ammonium groups being particularly useful.

The ion exchange resin employed in the present invention typically includes more than one anion. The anion may be selected from the group of bicarbonate, bisulfite, metalate and carboxylate anions, with a bicarbonate anion being particularly useful. When the anion is a carboxylate anion, the anion may be a polycarboxylic acid anion having in its chain molecule one or more carboxyl groups and one or more carboxylate groups, the individual carboxyl and/or carboxylate groups being separated from each other in the chain molecule by a separating group consisting of at least one atom. In certain instances, the polycarboxylic acid anion may be a citric acid derivative, more particularly a mono-anion of citric acid. In certain instances, the anion is a bicarbonate anion.

In one particular embodiment the solid ion exchange resin catalyst is a catalyst based on a quaternary ammonium resin, wherein the resin comprises a trimethylbenzyl ammonium group, and wherein the anion is a bicarbonate anion.

Because of the degree of divinyl benzene crosslinking present in the ion exchange resin, a balance is maintained between the water absorbing capacity of the resin and the elastic forces of the copolymer to keep the swollen resin in a stable moisture content. Typically, the ion exchange resin employed in the present invention has a water retention value that is from about 30% to about 80%, with a water retention value from about 40% to about 65% being even more typical.

Particularly useful in the present invention is a catalyst based on the strongly basic ion exchange resins in gel form including polystyrene that is crosslinked with from about 4 to about 8 wt. % divinyl benzene crosslinking and that has from 40% to 60% water retention, with the ion exchange resin including at least one of quaternary ammonium groups or quaternary phosphonium groups. Type I gel form ion exchange resins containing trimethyl ammonium groups are particularly useful. Furthermore, the catalysts may have capacities of about 1.0 eq/L to about 1.5 eq/L, more particularly from about 1.2 eq/L to about 1.3 eq/L. Such catalysts formed so that they are configured as substantially spherical beads having a particle size of from about 0.2 mm to about 1.5 mm have provided successful transesterification when used in combination with homogeneous, non-halogen-containing carbonation catalysts. Those having a particle size of from 0.3 mm to 1.3 mm may be particularly useful.

While the above-described specialized ion exchange resin is useful in the integrated process, any ion exchange resin useful for the transesterification reactions described herein may be used, such as those described earlier.

MOF catalysts may also be used in the transesterification reaction. The MOF catalysts may be the same as those used in the carbonation, as previously described, but under different reaction conditions. Further MOF catalysts useful for transesterification are described, for example, in Yinxi Zhou, "Metal-Organic Frameworks as an Acid Catalyst for the Synthesis of Ethyl Methyl Carbonate via Transesterification," *Journal of Molecular Catalysis A: Chemical*, pp 68-72 (2009), which is incorporated herein by reference in its entirety for all purposes.

The heterogeneous ion exchange resins and MOF transesterification catalysts described herein are typically employed in a catalyst bed contained in a reactor vessel. Various reactors may be used for the transesterification process, such as plug flow, fluidized bed, and reactive distillation type reactors, having one or more catalyst beds or reaction zones. Those reactors described in U.S. Pat. No. 7,663,005 may also be used for the transesterification reactions. One or more reactors, used in series or parallel, may be used for the transesterification reactions. A combination of the different homogeneous, IER and MOF catalysts described herein may also be used in the same or different reactors, as well.

Typical transesterification reaction conditions include a temperature range of from about 50° C. to about 250° C., with from about 120° C. to about 220° C. being typical. Reactor pressures may range from about 100 psig to about 1000 psig, more particularly from about 200 psig to about 500 psig. The aliphatic monohydric alcohol may be combined with the crude cyclic carbonate and introduced into the reactor. They may also be introduced separately. The aliphatic monohydric alcohol is typically used in an amount to provide an alcohol to cyclic carbonate molar feed ratio of from about 1:5 to about 3:1. A total feed LHSV of from about 1.0 to about 10 $hr^{-1}$ may be used in the transesterification reactor employing the ion exchange resin catalyst. For the MOF, a total feed LHSV of from about 1.0 to about 10 $hr^{-1}$ may be used in the transesterification reactor.

In particular embodiments, the reactant feed streams may be fed into or near the bottom of the reactor, with reaction products flowing upwardly through the catalyst bed(s) and reactor effluent being drawn from an outlet at or near the top of the reactor. In this way, the reactant mixture flows upward through the heterogeneous catalyst. This facilitates the collection of contaminant from being trapped in the catalyst bed, which frequently occurs with downflow reactors. In other embodiments, downflow or other reactor flow directions may be used.

As has been discussed, in an integrated process wherein a crude cyclo carbonate product is used in the transesterification reaction stage, the cyclic carbonation product is converted to dialkyl carbonate and diol products. As described earlier, in many applications the alkylene oxide used in the carbonation process is ethylene oxide, which yields ethylene carbonate. The ethylene carbonate, when reacted with methanol in the transesterification reaction yields dimethyl carbonate and ethylene glycol. In addition to these products, a large intermediate compound of hydromethylethyl carbonate (HEMC) is typically produced as a byproduct. When recycled back, the HEMC will further react with methanol to form dimethyl carbonate and ethylene glycol. Additionally, ethylene glycol can further react to form di-ethylene glycol, as well as tri-ethylene glycol and higher glycols.

After removal of the transesterification reaction products, dialkyl carbonate and diol products can be separated from each other and other compounds using known separation techniques. Other compounds from the reactor effluent may include unreacted cyclic carbonate, unreacted alcohol, the homogeneous catalyst, and various other byproducts, such as organic oxygenates and polyglycols.

FIG. 1 shows a schematic example of an integrated process system 10 for the production of dimethylcarbonate and monoethylene glycol from ethylene oxide. Such a system may also be used for the production of other dialkyl carbonates and diols using alkylene oxide starting materials, as will be apparent to those skilled in the art. As shown in FIG. 1, ethylene oxide 12 is fed into a carbonation reactor 14 containing a catalyst bed or beds 16 containing the MOF carbonation catalyst. Carbon dioxide 18 is also feed into the reactor 14. The reactants are fed into the reactor 14 under carbonation conditions, where the carbonation reaction takes place to convert the reactants into ethylene carbonate. The crude ethylene carbonate product is withdrawn from the reactor 14. The crude ethylene carbonate product, which will contain ethylene carbonate, and typically contains amounts of the homogeneous catalyst, unreacted ethylene oxide and other byproducts is removed from the reactor 14 through line 20. Volatile compounds may be removed from the reactor 14 through vent line 22. The crude ethylene carbonate product may be passed to a separator 24 where carbon dioxide and unreacted ethylene oxide may be removed via line 26 and recycled back to the reactor 14.

The remaining liquid crude ethylene carbonate product is removed from separator 24 through line 28 and is passed to transesterification reactor 30. Methanol is also introduced into the reactor 30 through line 32. As shown in the system 10, the methanol 32 and crude ethylene carbonate product 28 are fed into the bottom of the reactor 30 where they may be passed upwardly through a catalyst bed or beds 34 that may contain the ion exchange resin and/or MOF catalysts described herein. Alternatively, or in addition, homogeneous transesterification catalyst 36 as described herein may be introduced into the reactor 30, such as by combining with the feed stream 28. Product effluent is removed from the upper end of the reactor 30 through line 38. The product effluent will contain dimethyl carbonate, monoethylene glycol, unreacted methanol, unreacted ethylene carbonate, homogeneous catalyst and other by products. The transesterification products may undergo further processing and separation to remove product and to allow recycle of various compounds using known techniques.

The following examples better serve to illustrate the invention.

EXAMPLES

Example 1

Different MOF catalysts were evaluated for carbonation reactions to convert ethylene oxide (EO) into ethylene carbonate (EC). The catalysts used were aluminum terephthalate ($C_8H_5AlO_5$), available as Basolite® A100; copper benzene-1,3,5-tricarboxylate ($C_{18}H_6Cu_3O_{12}$), available as Basolite®

C300; and 2-methylimidazole zinc salt ($C_8H_{12}N_4Zn$), available as Basolite® Z1200, all from BASF SE and available through Sigma-Aldrich.

The carbonation reactions were performed in an Auto-Clave Engineering Batch Reactor. The typical carbonation reaction conditions used were those presented in Table 2 below:

TABLE 2

| Conditions | Typical |
| --- | --- |
| Temperature (° C.) | 150 or 200 |
| Pressure (psig) | Approx. 800 |
| EO Feed (liquid ml) | 100 |
| $CO_2$/EO (molar ratio) | 1.1-2.0 |
| Catalyst (wt. %) | 0.2 |

The MOF catalyst was weighed and directly added to the reactor cell of the autoclave prior to the installation of the cell to the reactor unit. EO in liquid form was then introduced into the cell from a feed tank on a balance, and the weight loss of the feed tank was the amount loaded into the reactor cell. Carbon dioxide ($CO_2$) was introduced as a gas at a pressure up to 850 psig. Under constant stirring at ≥200 rpm, the cell was heated to the desired reaction temperature, while $CO_2$ was supplied at constant pressure. After the steady-state of reaction was reached wherein the compositions of the liquid did not change anymore, as confirmed by gas chromatography (GC) analysis, the cell was further heated to a higher reaction temperature of 150° C. or 200° C.

During the reaction, samples were periodically taken via a dip tube in the reactor cell for GC analysis containing a known amount of acetone or methanol. Acetone and methanol were used as a solvent as well as an internal standard for GC analysis and calculation. The results for the MOF catalyst are presented in Table 3 below:

TABLE 3

| MOF Catalyst | Temp. (° C.) | EO Conversion | EC Selectivity |
| --- | --- | --- | --- |
| Basolite A100 | 150 | — | — |
| Basolite A100 | 200 | 24% | 55% |
| Basolite C300 | 150 | 1% | 100% |
| Basolite C300 | 200 | 26% | 100% |
| Basolite Z1200 | 150 | — | — |
| Basolite Z1200 | 200 | 26% | 100% |

Example 2

Transesterification reactions were performed in four liquid plug-flow reactors in parallel for different transesterification catalysts. The transesterification catalysts included homogeneous, IER and MOF catalysts. Each reactor consisted of a ½ inch OD and 12 inch long heated zone using a heating jacket. The reactor feed was a mixed solution of methanol and EC. The EC is solid at room temperature and so was dissolved approximately 24 hours before testing to take time to dissolve in the methanol. Butanol was also mixed with the EC/methanol solution in an amount of about 2.5 wt. % as an internal standard for the analysis of the feed and products. Butanol is well separated from other compounds and no new byproducts due to butanol were detected in testing.

The homogeneous transesterification catalysts used were those set forth in Table 4 below:

TABLE 4

| Catalyst | M.W. | pKa |
| --- | --- | --- |
| KOH | 56.11 | 14 |
| $KHCO_3$ | 100.12 | 6.35 |
| $K_2CO_3$ | 138.21 | 10.33 |

The IER catalysts were all characterized as strongly basic Type I ion exchange resins in gel form formed from polystyrene crosslinked with divinyl benzene having from about 4% to about 8% crosslinking, and from about 40% to about 60% water retention. The ion exchange resin included at least one of quaternary ammonium groups or quaternary phosphonium groups and were configured as substantially spherical beads having a particle size of from about 0.2 mm to about 1.5 mm. The IER catalysts were all commercially available catalysts designated as catalysts A-H.

The MOF transesterification catalysts used were aluminum terephthalate ($C_8H_5AlO_5$), available as Basolite® A100; copper benzene-1,3,5-tricarboxylate ($C_{18}H_6Cu_3O_{12}$), available as Basolite® C300; and 2-methylimidazole zinc salt ($C_8H_{12}N_4Zn$), available as Basolite® Z1200, all from BASF SE and available through Sigma-Aldrich.

For the heterogeneous catalysts (i.e. IER and MOF), 15 cc of catalyst was used and loaded on top of small glass beads in the reactor so that the whole bed was in the heated zone. For the homogeneous catalysts, about 0.2 wt. % or 0.2% of the catalyst by weight of the total feed was added and dissolved in the feed solution.

The typical transesterification reaction conditions used were those presented in Table 5 below:

TABLE 5

| Conditions | Typical |
| --- | --- |
| Catalyst (ml) for Heterogeneous process | 15 |
| Catalyst (wt. %) for Homogeneous | 0.02 or 0.1 |
| LHSV ($hr^{-1}$) for Heterogeneous | 4 |
| Feed Flow (ml/min) | 1.0 |
| Feed: CH3OH/EC (molar) | 4 |
| Temp. (C.) for Heterogeneous | 120 |
| Temp. (C.) for Homogeneous | 160 |
| Presssure (psig) | 300 |

During the reaction, samples were periodically taken for GC analysis. The products typically contained dimethyl carbonate (DMC), monoethylene glycol (MEG), 2-hydroxylethylmethyl carbonate (HEMC) and diethylene glycol (DEG). The results for each MOF catalyst are presented in Table 6 below:

TABLE 6

| Catalyst | Temp. (° C.) | EC Conversion % | DMC Selectivity % | MEG Selectivity % | HEMC Selectivity % | DEG Selectivity % |
| --- | --- | --- | --- | --- | --- | --- |
| Homogeneous | | | | | | |
| KOH (0.02%) | 120 | 50.0 | 98.2 | 97.7 | 1.7 | 0.6 |
| KOH (0.02%) | 120 | 50.1 | 98.4 | 97.8 | 1.5 | 0.7 |
| KOH (0.02%) | 120 | 50.6 | 98.3 | 98.4 | 1.6 | 0.0 |
| KHCO3 (0.02%) | 120 | 11.7 | 91.9 | 92.2 | 7.9 | 0.0 |
| KHCO3 (0.02%) | 140 | 19.9 | 100.0 | 100.0 | 0.0 | 0.0 |
| KHCO3 (0.02%) | 160 | 28.8 | 97.9 | 98.0 | 2.1 | 0.0 |
| KHCO3 (0.10%) | 120 | 31.4 | 97.5 | 96.1 | 2.4 | 1.6 |

TABLE 6-continued

| Catalyst | Temp. (°C.) | EC Conversion % | DMC Selectivity % | MEG Selectivity % | HEMC Selectivity % | DEG Selectivity % |
|---|---|---|---|---|---|---|
| KHCO3 (0.10%) | 140 | 45.3 | 100.0 | 100.0 | 0.0 | 0.0 |
| KHCO3 (0.10%) | 160 | 51.3 | 99.6 | 99.1 | 0.4 | 0.5 |
| K2CO3 (0.10%) | 120 | 59.0 | 99.6 | 96.7 | 0.7 | 2.7 |
| K2CO3 (0.10%) | 140 | 56.4 | 99.4 | 96.8 | 0.5 | 2.8 |
| IER | | | | | | |
| A | 120 | 56.9 | 95.6 | 95.3 | 4.4 | 0.6 |
| B | 120 | 56.9 | 95.4 | 95.2 | 4.6 | 0.6 |
| C | 120 | 57.8 | 96.0 | 95.7 | 4.0 | 0.6 |
| D | 120 | 56.5 | 94.7 | 94.7 | 5.3 | 0.7 |
| E | 120 | 54.9 | 96.6 | 96.3 | 3.4 | 0.6 |
| F | 120 | 55.9 | 95.0 | 95.1 | 5.0 | 0.6 |
| G | 120 | 55.9 | 95.0 | 95.1 | 5.0 | 0.6 |
| H | 120 | 58.0 | 92.2 | 92.9 | 7.8 | 0.2 |
| MOF | | | | | | |
| Z1200 | 120 | 46.0 | 97.7 | 96.8 | 2.7 | 0.0 |
| Z1200 | 150 | 57.3 | 98.9 | 98.5 | 1.3 | 0.0 |
| C300 | 120 | 1.1 | — | — | — | — |
| C300 | 150 | 2.1 | 28.5 | 34.4 | 68.4 | 0 |
| A100 | 120 | 4.3 | 12.4 | 17.1 | 85.4 | 0 |

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of forming dialkyl carbonate and diol products in an integrated process comprising:
reacting an alkylene oxide with carbon dioxide in the presence of a metal organic framework (MOF) catalyst with less than 0.5 mol % of any potassium or quaternary ammonium salts present based on moles of alkylene oxide feed present in a first reaction zone under reaction conditions to form a crude cyclic carbonate product; and
feeding the crude cyclic carbonate product from the first reaction zone wherein the crude carbonate product does not undergo any purification or separation, other than the optional removal of any portion of unreacted alkylene oxide, carbon dioxide, and light hydrocarbon gases, to a second reaction zone containing a transesterification catalyst along with an aliphatic monohydric alcohol and allowing the cyclic carbonate product and monohydric alcohol to react under reaction conditions to form the dialkyl carbonate and diol products.

2. The method of claim 1, wherein:
the alkylene oxide has the formula

wherein $R_1$ and $R_2$ are independently from one another a —$(CH_2)_m$— group, wherein m is an integer of from 1 to 3.

3. The method of claim 1, wherein:
the alkylene oxide is ethylene oxide and the cyclic carbonate product is ethylene carbonate.

4. The method of claim 1, wherein:
the MOF catalyst is used in the first reaction zone in an amount to provide a LHSV of from about 0.5 $hr^{-1}$ to about 10 $hr^{-1}$.

5. The method of claim 1, wherein:
the aliphatic monohydric alcohol is a $C_1$ to $C_5$ aliphatic monohydric alcohol.

6. The method of claim 1, wherein:
the monohydric alcohol is methanol.

7. The method of claim 1, wherein:
the MOF catalyst is at least one selected from aluminum terephthalate ($C_8H_5AlO_5$), copper benzene-1,3,5-tricarboxylate ($C_{18}H_6Cu_3O_{12}$), and 2-methylimidazole zinc salt ($C_8H_{12}N_4Zn$).

8. The method of claim 1, wherein:
the alkylene oxide is ethylene oxide and the aliphatic monohydric alcohol is methanol, and wherein the dialkyl carbonate includes dimethyl carbonate and the diol includes monoethylene glycol.

9. The method of claim 1, wherein:
the transesterification catalyst is at least one of an MOF catalyst, ion exchange resin, and a homogeneous catalyst.

10. The method of claim 1, wherein:
the transesterification catalyst is an MOF catalyst.

11. The method of claim 1, wherein:
the molar ratio of aliphatic monohydric alcohol to the crude cyclic carbonate product introduced into the second reaction zone is from about 1.5:1 to about 3:1.

12. The method of claim 1, wherein:
the transesterification catalyst is a strongly basic Type I ion exchange resin in gel form of polystyrene crosslinked with divinyl benzene having from about 4% to about 8% crosslinking, and from about 40% to about 60% water retention, the ion exchange resin including at least one of quaternary ammonium groups or quaternary phosphonium groups, the transesterification catalyst being configured as substantially spherical beads having a particle size of from about 0.2 mm to about 1.5 mm.

13. The method of claim 12, wherein:
the ion exchange resin includes an anion selected from the group consisting of bicarbonate, bisulfite, metalate, carboxylate, and halide.

14. The method of claim 1, wherein:
the transesterification catalyst is a strongly basic homogeneous catalyst having a pKa value of 5 or more.

15. The method of claim 1, wherein:
the MOF catalyst is used in an amount to provide a LHSV f from about 0.5 $hr^{-1}$ to about 10 $hr^{-1}$.

16. A method of forming dialkyl carbonate and diol products in an integrated process comprising:
reacting an ethylene oxide with carbon dioxide in the presence of a metal organic framework (MOF) catalyst with less than 0.5 mol % of any potassium or quaternary ammonium salts present based on moles of ethylene oxide feed present in a first reaction zone under reaction conditions to form a crude ethylene carbonate product; and
feeding the crude ethylene carbonate product from the first reaction zone wherein the crude ethylene carbonate product does not undergo any purification or separation, other than the optional removal of any portion of unreacted ethylene oxide, carbon dioxide, and light hydrocarbon gases, to a second reaction zone containing a transesterification catalyst along with an aliphatic monohydric alcohol and allowing the ethylene carbonate product and monohydric alcohol to react under reaction conditions to form the dialkyl carbonate and diol products.

17. The method of claim 16, wherein:
the MOF catalyst is at least one selected from aluminum terephthalate ($C_8H_5AlO_5$), copper benzene-1,3,5-tricarboxylate ($C_{18}H_6Cu_3O_{12}$), and 2-methylimidazole zinc salt ($C_8H_{12}N_4Zn$).

18. The method of claim 16, wherein:
the MOF catalyst is used in the first reaction zone in an amount to provide a LHSV of from about 0.5 $hr^{-1}$ to about 10 $hr^{-1}$.

19. The method of claim 16, wherein:
the aliphatic monohydric alcohol is a $C_1$ to $C_5$ aliphatic monohydric alcohol.

20. The method of claim 16, wherein:
the monohydric alcohol is methanol.

21. The method of claim 16, wherein:
the aliphatic monohydric alcohol is methanol, and wherein the dialkyl carbonate includes dimethyl carbonate and the diol includes monoethylene glycol.

22. The method of claim 16, wherein:
the transesterification catalyst is at least one of an MOF catalyst, ion exchange resin, and a homogeneous catalyst.

23. The method of claim 16, wherein:
the transesterification catalyst is an MOF catalyst.

24. The method of claim 16, wherein:
the molar ratio of aliphatic monohydric alcohol to the crude ethylene carbonate product introduced into the second reaction zone is from about 1.5:1 to about 3:1.

25. The method of claim 16, wherein:
the transesterification catalyst is a strongly basic Type I ion exchange resin in gel form of polystyrene crosslinked with divinyl benzene having from about 4% to about 8% crosslinking, and from about 40% to about 60% water retention, the ion exchange resin including at least one of quaternary ammonium groups or quaternary phosphonium groups, the transesterification catalyst being configured as substantially spherical beads having a particle size of from about 0.2 mm to about 1.5 mm.

26. The method of claim 25, wherein:
the ion exchange resin includes an anion selected from the group consisting of bicarbonate, bisulfite, metalate, carboxylate, and halide.

\* \* \* \* \*